(12) United States Patent
Marash

(10) Patent No.: US 11,058,373 B2
(45) Date of Patent: Jul. 13, 2021

(54) IRRADIATION TREATMENT SYSTEM AND METHOD

(71) Applicant: Sino-Israeli Health Alliance International Medical Technology Co., Ltd., Shandong (CN)

(72) Inventor: Michael Marash, Rishon Le'tzion (IL)

(*) Notice: Subject to any disclaimer, the term of this patent is extended or adjusted under 35 U.S.C. 154(b) by 138 days.

(21) Appl. No.: 16/488,587

(22) PCT Filed: Dec. 16, 2018

(86) PCT No.: PCT/IL2018/051359
§ 371 (c)(1),
(2) Date: Aug. 25, 2019

(87) PCT Pub. No.: WO2019/123452
PCT Pub. Date: Jun. 27, 2019

(65) Prior Publication Data
US 2020/0289071 A1    Sep. 17, 2020

Related U.S. Application Data

(60) Provisional application No. 62/608,579, filed on Dec. 21, 2017.

(51) Int. Cl.
*A61B 6/08*      (2006.01)
*A61B 6/00*      (2006.01)
(Continued)

(52) U.S. Cl.
CPC .............. *A61B 6/4092* (2013.01); *A61B 6/04* (2013.01); *A61B 6/4464* (2013.01);
(Continued)

(58) Field of Classification Search
CPC ....... A61B 6/4092; A61B 6/04; A61B 6/4464; A61N 5/1049; A61N 5/1077;
(Continued)

(56) References Cited

U.S. PATENT DOCUMENTS

| 2009/0314961 A1 | 12/2009 | Balakin |
| 2011/0147608 A1 | 6/2011 | Balakin |

(Continued)

FOREIGN PATENT DOCUMENTS

| WO | 2014103471 A1 | 7/2014 |
| WO | 2015071430 A1 | 5/2015 |

OTHER PUBLICATIONS

International search report for parent PCT application PCT/IL2018/051359, issued by USPTO dated Apr. 11, 2019.
(Continued)

*Primary Examiner* — David P Porta
*Assistant Examiner* — Mamadou Faye
(74) *Attorney, Agent, or Firm* — The Roy Gross Law Firm, LLC; Roy Gross

(57) ABSTRACT

An irradiation treatment system comprising: a synchrotron ring defining a border extending vertically from the synchrotron ring; a particle beam generator, an output of the particle beam generator coupled to an inlet of the synchrotron ring and arranged to inject charged particle beams into the synchrotron ring; a field control unit arranged to adjust an electric and magnetic field such that the injected charged particle beams are accelerated; a treatment irradiation source positioned within the defined border, the input of the irradiation source coupled to the outlet of the synchrotron ring and arranged to receive the accelerated particle beams from the synchrotron ring; and a patient support member positioned within the defined border and arranged to support a patient in a predetermined relationship with the output of the treatment irradiation source, the treatment irradiation source arranged to irradiate the supported patient with the accelerated particle beams.

16 Claims, 3 Drawing Sheets

(51) Int. Cl.
*A61B 6/04* (2006.01)
*A61N 5/10* (2006.01)

(52) U.S. Cl.
CPC ......... *A61N 5/1049* (2013.01); *A61N 5/1077* (2013.01); *A61N 2005/1087* (2013.01)

(58) Field of Classification Search
CPC ......... A61N 2055/1087; A61N 5/1087; H05H 2007/002; H05H 7/001
See application file for complete search history.

(56) References Cited

U.S. PATENT DOCUMENTS

| | | |
|---|---|---|
| 2011/0284762 A1 | 11/2011 | Balakin |
| 2011/0313232 A1 | 12/2011 | Balakin |
| 2015/0258350 A1 | 9/2015 | Balakin et al. |
| 2016/0279443 A1* | 9/2016 | Bennett ................ A61N 5/1077 |
| 2017/0014646 A1 | 1/2017 | Lee et al. |

OTHER PUBLICATIONS

Written opinion on international search report for parent PCT application PCT/IL2018/051359, issued by USPTO dated Apr. 11, 2019.

* cited by examiner

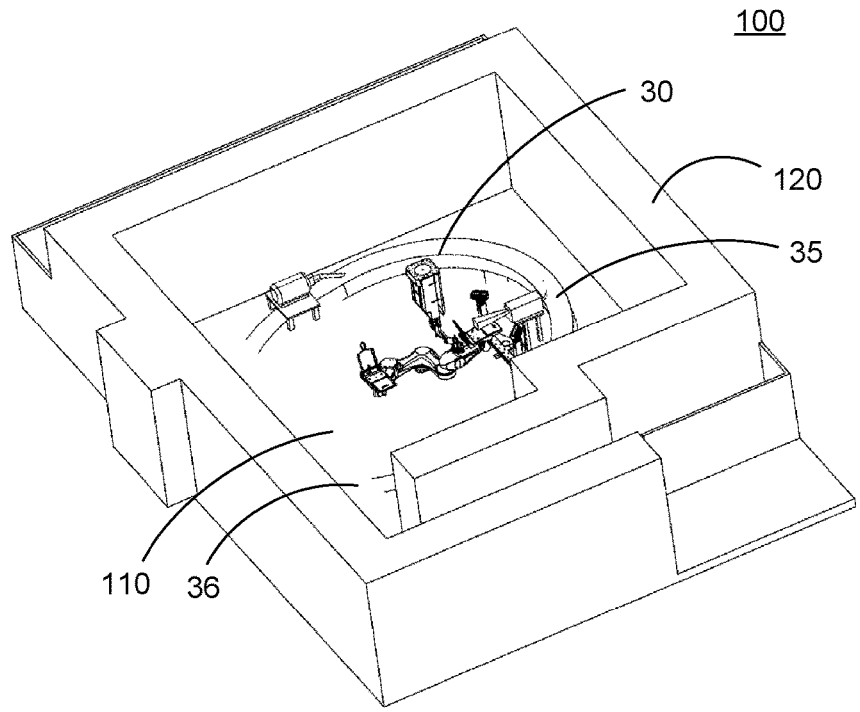

FIG. 2D

| 1000 | SUPPORT A PATIENT IN A PREDETERMINED RELATIONSHIP WITH AN OUTPUT OF A TREATMENT IRRADIATION SOURCE, OPT. IRRADIATION SOURCE POSITIONED ABOVE PATIENT |
|---|---|
| 1010 | CONTROL IRRADIATION SOURCE TO IRRADIATE PATIENT WITH PARTICLE BEAMS ACCELERATED WITHIN A SYNCHROTRON RING, A RING PERIMETER DEFINING A SPACE EXTENDED VERTICALLY FROM THE RING PERIMETER, EACH OF THE PATIENT AND IRRADIATION SOURCE POSITIONED WITHIN THE DEFINED SPACE, OPT. A SECOND RING PORTION HEIGHER THAN A FIRST RING PORTION, OPT. THE FIRST PORTION EMBEDDED IN THE FLOOR, OPT. THE SECOND PORTION EMBEDDED IN THE CEILING OPPOSING THE FLOOR, OPT. THE RING POSITIONED ABOVE PATIENT, OPT. THE RING POSITIONED BELOW PATIENT |
| 1020 | (OPT.) CONTROL AN IMAGER TO IMAGE PATIENT, IMAGER POSITIONED WITHIN DEFINED SPACE |

FIG. 3

IRRADIATION TREATMENT SYSTEM AND METHOD

CROSS-REFERENCE TO RELATED APPLICATIONS

The current application claims priority from U.S. provisional patent application Ser. No. 62/608,579, filed Dec. 21, 2017 and entitled "IRRADIATION TREATMENT SYSTEM", the entire contents of which are incorporated herein by reference.

TECHNICAL FIELD

The invention relates generally to the field of teletherapy and in particular to an irradiation treatment arrangement.

BACKGROUND

Teletherapy is defined as a treatment methodology in which an irradiation source is at a distance from the body to be treated. X-rays and electron beams have long been used in teletherapy to treat various cancers. Unfortunately, X-rays exhibit a linear energy transfer approaching an exponential attenuation function, and are therefore of minimal safe use for deeply embedded growths. The use of heavy particles, particularly hadrons and more particularly protons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy. For clarity, this document will describe treatment as being accomplished with protons, however this is not meant to be limiting in any way.

The protons or ions can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

A synchrotron is a type of cyclic particle accelerator in which a magnetic field is used to turn the particles so they circulate and an electric field is used to accelerate the particles. The synchrotron is named due to its synchronization of the applied fields with the travelling particle beam.

By increasing the applied magnetic fields appropriately as the particles gain energy, the charged particles path is held constant as the charged particles are accelerated, allowing the vacuum container for the particles to be a large torus, i.e. a synchrotron ring. Typically, it is easier to use some straight sections between the bending magnets and some turning sections giving the torus the shape of a round-cornered polygon.

The ability of a synchrotron to accelerate particles is limited by the fact that the particles must be charged to be accelerated at all, but charged particles under acceleration emit photons, thereby losing energy. The beam energy limit is reached when the energy lost to the lateral acceleration required to maintain the beam path in a circle equals the energy added each cycle. One way of increasing the beam energy limit is by using a synchrotron ring with a larger radius.

FIG. 1 illustrates a high level perspective view of an irradiation treatment system 10, irradiation treatment system 10 comprising: a particle beam generator 20; a synchrotron ring 30; a field control unit 40; a treatment irradiation source 50, comprising a nozzle 55; a patient support member 60; and an optional imager 70. Synchrotron ring 30 exhibits an inlet 31 an outlet 32 and an outer perimeter 33. Outer perimeter 33 defines a space 34 extending vertically therefrom. Specifically, space 34 defines a vertical column whose center axis intersects the center enclosed by synchrotron ring 30 and whose perimeter is defined by outer perimeter 33. An output of particle beam generator 20 is coupled to inlet 31 of synchrotron ring 30 and an input of treatment irradiation source 50 is coupled to outlet 32 of synchrotron ring 30. Particle beam generator 20, treatment irradiation source 50, patient support member 60 and optional imager 70 are positioned outside space 34. Patient support member 60 is positioned in relation to treatment irradiation source 50 such that a patient (not shown) supported by patient support member 60 can be irradiated thereby, as will be described below. In one embodiment, field control unit 40 is positioned within the center of space 34.

In operation, particle beam generator 20 generates charged particle beams and outputs the generated charged particle beams into synchrotron ring 30 via inlet 31. Particle beam generator 20 further provides initial acceleration for the charged particle beams, prior to their input into synchrotron ring 30. Field control unit 40 controls the electric and magnetic fields of synchrotron ring 30 to provide further acceleration for the charged particle beams, as known to those skilled in the art at the time of the invention. The accelerated particle beams are output from synchrotron ring 30, via outlet 32, into treatment irradiation source 50 and the accelerated particle beams are output via nozzle 55. A patient supported by patient support member 60 is positioned in a predetermined relationship with nozzle 55 such that the output particle beams irradiate a treatment target of the patient, as described above. In one embodiment, prior to the irradiation, optional imager 70 images the patient supported by patient support member 60 and the position of the patient is adjusted accordingly, as described above.

As described above, a synchrotron ring 30 exhibiting a large radius is desired so as to increase the energy of the accelerated particle beams. This requires a very large treatment room in order to accommodate the large synchrotron ring 30, along with treatment irradiation source 50, patient support member 60 and optional imager 70.

US patent application publication S/N US 2009/0314961, published on Dec. 24, 2009, to Balakin, the entire contents of which are incorporated herein by reference, reduces the overall size of the synchrotron ring by using an intensity feedback loop to improve the efficiency of the synchrotron, thereby allowing to reduce the radius of the synchrotron ring while achieving the same acceleration. Unfortunately, such a solution adds additional complexity and cost to the system.

SUMMARY OF THE INVENTION

Accordingly, it is a principal object of the present invention to overcome disadvantages of prior art methods and arrangements of teletherapy. This is provided in the present invention by an irradiation treatment system comprising: a synchrotron ring exhibiting an inlet and an outlet, the synchrotron ring defining a border extending vertically from the synchrotron ring; a particle beam generator, an output of the particle beam generator coupled to the inlet of the synchrotron ring and arranged to inject charged particle beams into the synchrotron ring; a field control unit arranged to adjust an electric and magnetic field such that the injected charged particle beams are accelerated within the synchrotron ring; a treatment irradiation source positioned within the defined border and comprising an input and an output, the input of the irradiation source coupled to the outlet of the synchrotron ring and arranged to receive the accelerated particle beams from the synchrotron ring; and a patient support member positioned within the defined border and arranged to support a patient in a predetermined relationship with the output of the treatment irradiation source, the treatment irradiation source arranged to irradiate the supported patient with the accelerated particle beams.

In one embodiment, wherein the synchrotron ring exhibits a first portion and a second portion opposing the first portion, the first portion of the synchrotron ring exhibiting a first height in relation to a floor and the second portion of the synchrotron ring exhibiting a second height in relation to the floor, wherein the second height is greater than the first height. In one further embodiment, the first portion of the synchrotron ring is embedded in the floor. In another further embodiment, the second portion of the synchrotron is embedded in a ceiling opposing the floor.

In another embodiment, the synchrotron ring is positioned above the patient support member. In one further embodiment, the treatment irradiation source is positioned above the patient support member.

In one embodiment, the synchrotron ring is positioned below the patient support member. In another embodiment, the irradiation system further comprises an imager positioned within the defined space, the imager arranged to image the patient.

In one independent embodiment, an irradiation treatment method is provided, the method comprising: supporting a patient in a predetermined relationship with an output of a treatment irradiation source; and controlling the treatment irradiation source to irradiate the supported patient with particle beams accelerated within a synchrotron ring, a perimeter of the synchrotron ring defining a space extended vertically from the ring perimeter, wherein each of the supported patient and the treatment irradiation source is positioned within the defined space.

In one embodiment, the synchrotron ring exhibits a first portion and a second portion opposing the first portion, the first portion of the synchrotron ring exhibiting a first height in relation to a floor and the second portion of the synchrotron ring exhibiting a second height in relation to the floor, wherein the second height is greater than the first height. In one further embodiment, the first portion of the synchrotron ring is embedded in the floor. In another further embodiment, the second portion of the synchrotron is embedded in a ceiling opposing the floor.

In another embodiment, the synchrotron ring is positioned above the supported patient. In one further embodiment, the treatment irradiation source is positioned above the supported patient.

In one embodiment, the synchrotron ring is positioned below the supported patient. In another embodiment, the method further comprises controlling an imager to image the positioned patient, wherein the imager is positioned within the defined space.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 3 illustrates a high level flow chart of an irradiation treatment method, in accordance with certain embodiments.

DETAILED DESCRIPTION OF THE PREFERRED EMBODIMENTS

Figure 1:
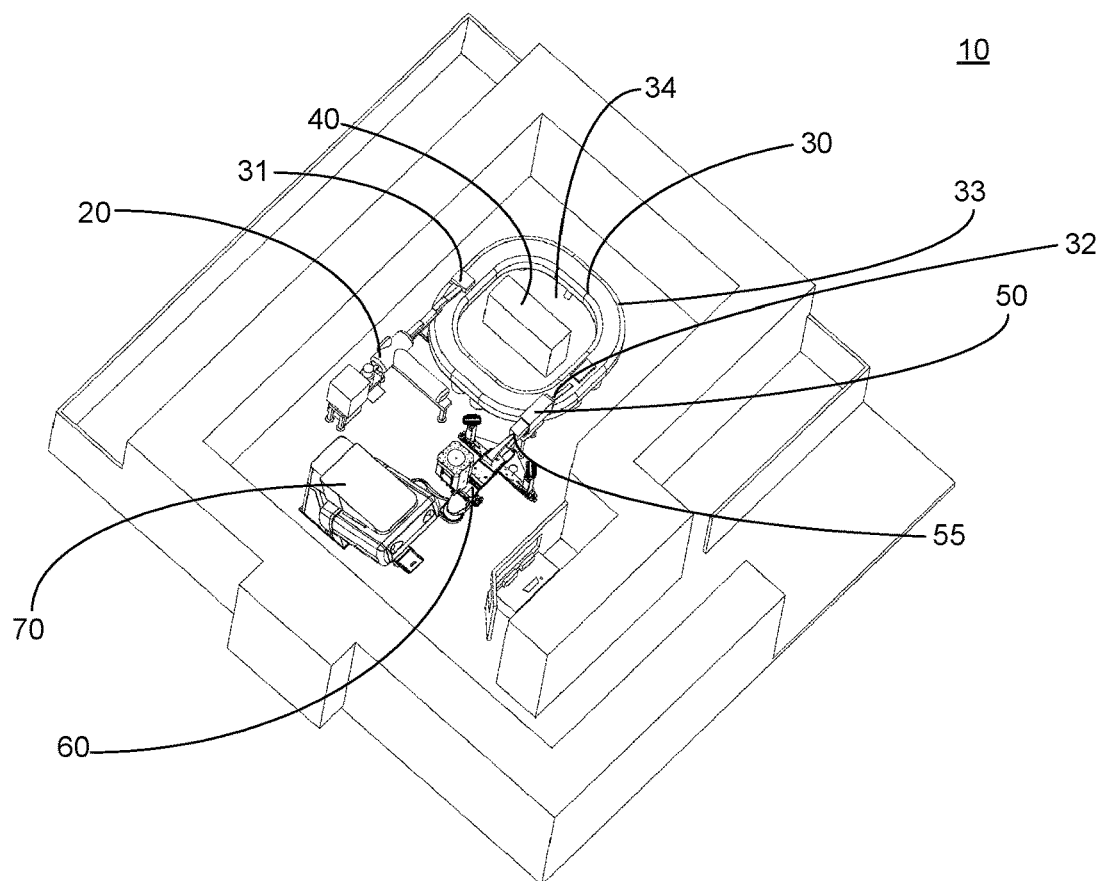
FIG. 1 illustrates a high level perspective view of a prior art irradiation treatment system.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 2A:
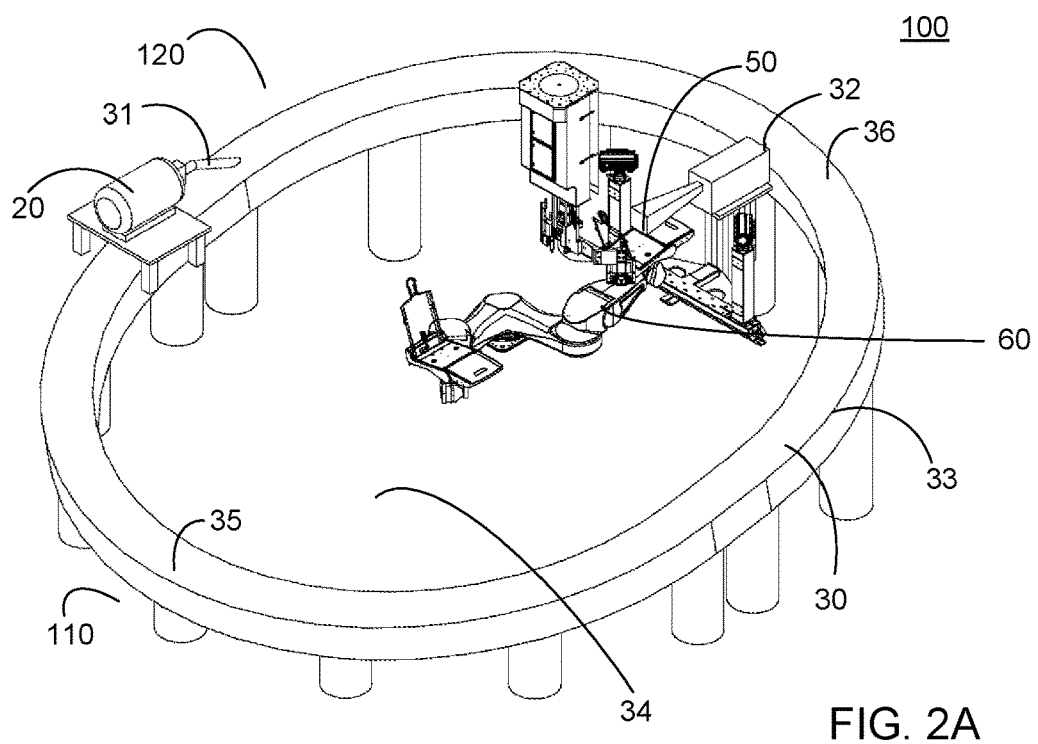
FIG. 2 illustrates a high level perspective view of an irradiation treatment system, in accordance with certain embodiments.
Figure 2B:
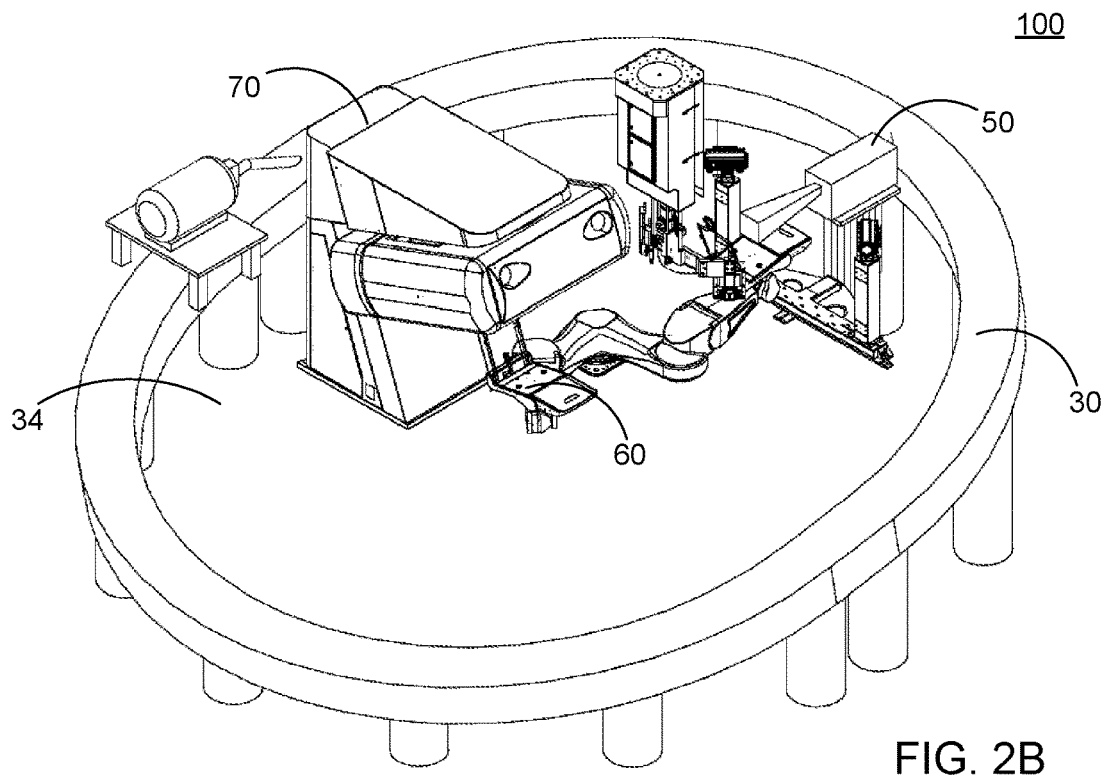
Figure 2C:
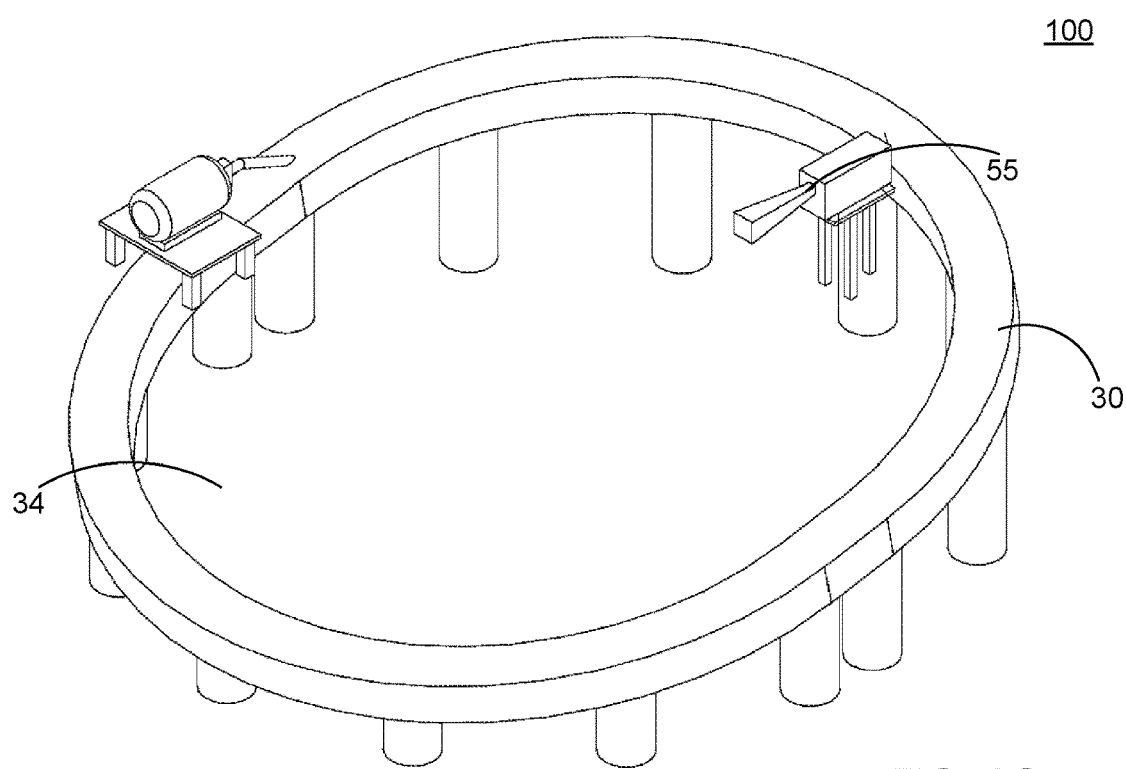

FIGS. 2A-2D illustrate various high level perspective views of an irradiation treatment system 100. Irradiation treatment system 100 comprises: a particle beam generator 20; a synchrotron ring 30; a field control unit 40 (not shown); a treatment irradiation source 50, comprising a nozzle 55; a patient support member 60; and an optional imager 70. For simplicity, only a portion of particle beam generator 20 is shown. In FIGS. 2A-2D: FIG. 2A illustrates a high level perspective view of irradiation treatment system 100 without optional imager 70; FIG. 2B illustrates a high level perspective view of irradiation treatment system 100 with optional imager 70; FIG. 2C illustrates a high level perspective view of particle beam generator 20, synchrotron ring 30 and nozzle 55; and FIG. 2D illustrates an embodiment of irradiation treatment system 100 wherein a portion of synchrotron ring 30 is embedded in a floor of a treatment room. FIGS. 2A-2D are described herein together.

Synchrotron ring 30 exhibits an inlet 31 an outlet 32 and an outer perimeter 33. In one embodiment, as illustrated, synchrotron ring 30 further exhibits a first portion 35 and a second portion 36 opposing first portion 35. First portion 35 exhibits a first height in relation to a level floor 110 of a treatment room 120 and second portion 36 exhibits a second height in relation to level floor 110 of treatment room 120. The second height is greater than the first height, i.e. synchrotron ring 30 is on an angle. In one further embodiment, as illustrated in FIG. 2D, first portion 35 of synchrotron ring 30 is embedded in floor 100. In another further embodiment, the second height is at least 170 centimeters, so as to allow a patient to pass under second portion 36. In another further embodiment (not shown), second portion 36 of synchrotron ring 30 is embedded into the ceiling of treatment room 120. In another embodiment (not shown), synchrotron ring 30 hangs from the ceiling of treatment room 120. In yet another embodiment (not shown), synchrotron ring 30 is positioned on the floor above treatment room 120. In yet another embodiment (not shown), the entirety of synchrotron ring 30 is embedded in floor 100.

Outer perimeter 33 defines a space 34 extending vertically therefrom. Specifically, space 34 defines a vertical column whose center axis intersects the center enclosed by synchrotron ring 30 and whose perimeter is defined by outer perimeter 33. Particularly, space 34 extends vertically between floor 100 and the ceiling of treatment room 120, regardless of the angle of synchrotron ring 30.

An output of particle beam generator 20 is coupled to inlet 31 of synchrotron ring 30 and an input of treatment irradiation source 50 is coupled to outlet 32 of synchrotron ring 30. Particle beam generator 20, field control unit 40, treatment irradiation source 50, patient support member 60 and optional imager 70 are positioned within space 34. Patient support member 60 is positioned in relation to treatment irradiation source 50 such that a patient (not shown) supported by patient support member 60 can be irradiated thereby, as described above. In one embodiment, as described above, synchrotron ring 30 is positioned above patient support member 60. Alternatively, in another embodiment, synchrotron ring 30 is positioned below patient support member 60.

In operation, as described above, particle beam generator 20 generates charged particle beams and outputs the generated charged particle beams into synchrotron ring 30 via inlet 31. Particle beam generator 20 further provides initial acceleration for the charged particle beams, prior to their input into synchrotron ring 30. Field control unit 40 controls the electric and magnetic fields of synchrotron ring 30 to provide further acceleration for the charged particle beams, as known to those skilled in the art at the time of the invention. The accelerated particle beams are output from synchrotron ring 30, via outlet 32, into treatment irradiation source 50 and the accelerated particle beams are output via nozzle 55. A patient supported by patient support member 60 is positioned in a predetermined relationship with nozzle 55 such that the output particle beams irradiate a treatment target of the patient, as described above. In one embodiment, prior to the irradiation, optional imager 70 images the patient supported by patient support member 60 and the position of the patient is adjusted accordingly, as described above.

Advantageously, by positioning treatment irradiation source 50, patient support member 60 and optional imager 70 within defined space 34, the size of treatment room 120 can be reduced. Additionally, in the embodiment where synchrotron ring 30, or a second portion 36 thereof is raised above patient support member 60, nozzle 55 of treatment irradiation source 50 can be placed at any angle for irradiating the patient, including a vertical position in relation to the patient.

FIG. 3 illustrates a high level flow chart of an irradiation treatment method, in accordance with certain embodiments.

In stage 1000, a patient is supported in a predetermined relationship with an output of a treatment irradiation source. Optionally, the treatment irradiation source is positioned above the supported patient. In stage 1010, the treatment irradiation source of stage 1000 irradiates the supported patient with particle beams accelerated within a synchrotron ring, a perimeter of the synchrotron ring defining a space extended vertically from the ring perimeter. Both the supported patient and the treatment irradiation source of stage 1000 are positioned within the defined space. Particularly, in one embodiment, the patient is supported on a patient support member, the patient support member being positioned within the defined space.

In another embodiment, the synchrotron ring exhibits a first portion and a second portion, the second portion opposing the first portion. The first portion of the synchrotron ring exhibits a first height in relation to a floor and the second portion of the synchrotron ring exhibits a second height in relation to the floor, the second height being greater than the first height. Particularly, in one embodiment, the height is measured in relation to the floor level, i.e. a plane parallel to sea level which defines the height of the floor in relation to the bottom of the building, disregarding any irregularities or angles of the floor. In one embodiment, the first portion of the synchrotron ring is embedded in the floor. In another embodiment, the second portion of the synchrotron ring is embedded in a ceiling opposing the floor. In one further embodiment, the first portion of the synchrotron ring is embedded in the floor, while the second portion of the synchrotron ring is not embedded in the ceiling opposing the floor. In another further embodiment, the first portion of the synchrotron ring is not embedded in the floor, while the second portion of the synchrotron ring is embedded in the ceiling opposing the floor. In another further embodiment, the first portion of the synchrotron ring is embedded in the floor and the second portion of the synchrotron ring is embedded in the ceiling opposing the floor.

In one embodiment, the synchrotron ring is positioned above the supported patient. In another embodiment, the synchrotron ring is positioned below the supported patient.

In stage 1020, an imager is controlled to image the supported patient of stage 1000. The imager is positioned within the defined space of stage 1010.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. An irradiation treatment system comprising:
   a synchrotron ring exhibiting an inlet and an outlet and a perimeter, said synchrotron ring perimeter defining a space extended vertically from said ring perimeter;
   a particle beam generator, an output of said particle beam generator coupled to said inlet of said synchrotron ring and arranged to inject charged particle beams into said synchrotron ring;
   a field control unit arranged to adjust an electric and magnetic field such that said injected charged particle beams are accelerated within said synchrotron ring;
   a treatment irradiation source positioned within said defined space and comprising an input and an output, said input of said irradiation source coupled to said outlet of said synchrotron ring and arranged to receive said accelerated particle beams from said synchrotron ring; and
   a patient support member positioned within said defined space and arranged to support a patient in a predetermined relationship with said output of said treatment irradiation source, said treatment irradiation source arranged to irradiate said supported patient with said accelerated particle beams.

2. The irradiation treatment system of claim 1, wherein said synchrotron ring exhibits a first portion and a second portion opposing said first portion, said first portion of said synchrotron ring exhibiting a first height in relation to a floor and said second portion of said synchrotron ring exhibiting a second height in relation to the floor,
   wherein said second height is greater than said first height.

3. The irradiation treatment system of claim 2, wherein said first portion of said synchrotron ring is embedded in the floor.

4. The irradiation treatment system of claim 2, wherein said second portion of said synchrotron is embedded in a ceiling opposing the floor.

5. The irradiation treatment system of claim 1, wherein said synchrotron ring is positioned above said patient support member.

6. The irradiation treatment system of claim 5, wherein said treatment irradiation source is positioned above said patient support member.

7. The irradiation treatment system of claim 1, wherein said synchrotron ring is positioned below said patient support member.

8. The irradiation treatment system of claim 1, further comprising an imager positioned within said defined space, said imager arranged to image the patient.

9. An irradiation treatment method, the method comprising:
   supporting a patient in a predetermined relationship with an output of a treatment irradiation source; and
   controlling the treatment irradiation source to irradiate said supported patient with particle beams accelerated within a synchrotron ring, a perimeter of the synchrotron ring defining a space extended vertically from the ring perimeter,
   wherein each of said supported patient and the treatment irradiation source is positioned within said defined space.

10. The irradiation treatment method of claim 9, wherein the synchrotron ring exhibits a first portion and a second portion opposing the first portion, the first portion of the synchrotron ring exhibiting a first height in relation to a floor and the second portion of said synchrotron ring exhibiting a second height in relation to the floor,
    wherein the second height is greater than the first height.

11. The irradiation treatment method of claim 10, wherein the first portion of said synchrotron ring is embedded in the floor.

12. The irradiation treatment method of claim 10, wherein the second portion of said synchrotron is embedded in a ceiling opposing the floor.

13. The irradiation treatment method of claim 9, wherein the synchrotron ring is positioned above said supported patient.

14. The irradiation treatment method of claim 13, wherein the treatment irradiation source is positioned above said supported patient.

15. The irradiation treatment method of claim 9, wherein the synchrotron ring is positioned below said positioned patient.

16. The irradiation treatment method of claim 9, further comprising controlling an imager to image said supported patient,
    wherein the imager is positioned within the defined space.

* * * * *